United States Patent
Heidrich et al.

(10) Patent No.: US 8,823,947 B2
(45) Date of Patent: Sep. 2, 2014

(54) OPTICAL SENSOR AND METHOD FOR DETECTING MOLECULES

(75) Inventors: Helmut Heidrich, Berlin (DE); Peter Lútzow, Berlin (DE); Herbert Venghaus, Berlin (DE); Hugo Joseph Wilhelmus Maria Hoekstra, la Hengelo (NL)

(73) Assignee: Fraunhofer-Gesellschaft zur Förderung der angewandten Forschung e.V. (DE)

( * ) Notice: Subject to any disclaimer, the term of this patent is extended or adjusted under 35 U.S.C. 154(b) by 418 days.

(21) Appl. No.: 13/382,267

(22) PCT Filed: Jun. 18, 2010

(86) PCT No.: PCT/EP2010/003784
§ 371 (c)(1),
(2), (4) Date: Apr. 4, 2012

(87) PCT Pub. No.: WO2011/000494
PCT Pub. Date: Jan. 6, 2011

(65) Prior Publication Data
US 2012/0182552 A1    Jul. 19, 2012

(30) Foreign Application Priority Data
Jul. 1, 2009    (EP) .................................... 09075286

(51) Int. Cl.
*G01B 9/02*    (2006.01)
(52) U.S. Cl.
USPC ............................................ 356/480; 385/12
(58) Field of Classification Search
CPC ........ G01N 21/00; G01N 21/17; G01N 21/31
USPC .................... 356/480, 454; 385/12
See application file for complete search history.

(56) References Cited

U.S. PATENT DOCUMENTS

| 5,663,790 A | 9/1997 | Ekstroem et al. |
| 6,721,053 B1 * | 4/2004 | Maseeh .......................... 356/436 |

(Continued)

FOREIGN PATENT DOCUMENTS

WO    WO-2008/141417 A1    11/2008

OTHER PUBLICATIONS

"International Application No. PCT/EP2010/003784, International Preliminary Report on Patentability mailed Jan. 12, 2012", 7 pgs.

(Continued)

*Primary Examiner* — Jonathan Hansen
(74) *Attorney, Agent, or Firm* — Schwegman Lundberg & Woessner, P.A.

(57) ABSTRACT

The invention relates to an optical sensor comprising an optical waveguide (1) and a light-sensitive element (4) for detecting light coupled out of the waveguide (1) and also various ring resonators (2), the ring resonators (2) being coupled optically to the mentioned waveguide (1) and, with the exception of at most one of the ring resonators (2), each having a means (5) for adjusting resonance frequencies of the respective ring resonator (2) and/or of the coupling between the ring resonator (2) and the waveguide (1) and at least two of the ring resonators (2) having different optical lengths in an initial state and being disposed for having their resonance frequencies influenced by means of different variables to be measured which are specific for each of these ring resonators (2). The invention refers furthermore to a method which can be implemented with a sensor of this type for detecting molecules of at least one substance.

14 Claims, 3 Drawing Sheets

(56) References Cited

U.S. PATENT DOCUMENTS

Figure 1:
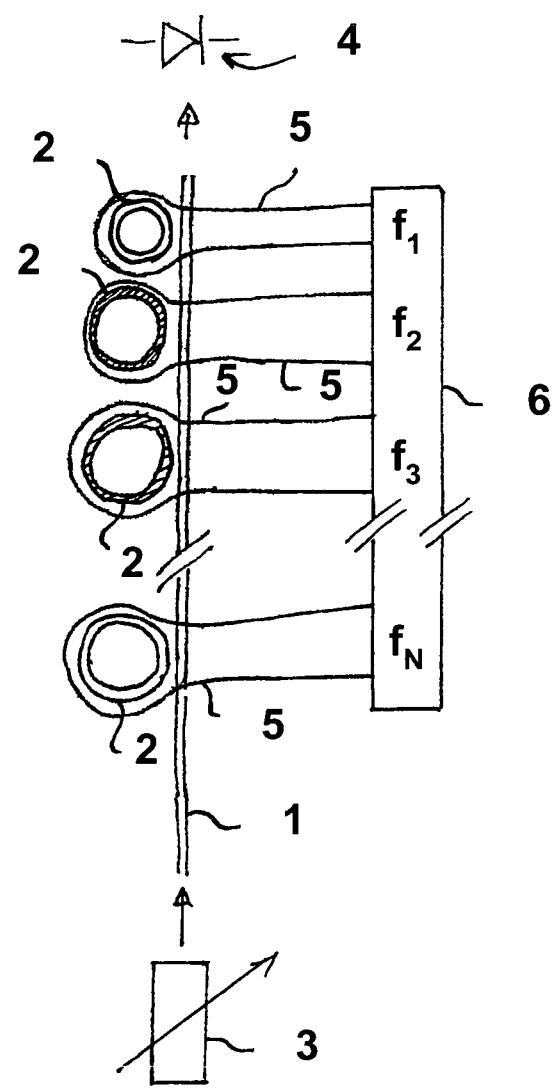

| | | |
|---|---|---|
| 7,145,660 B2 | 12/2006 | Margalit et al. |
| 2003/0231826 A1 | 12/2003 | Boyd et al. |
| 2004/0023396 A1 | 2/2004 | Boyd et al. |
| 2004/0146431 A1 | 7/2004 | Scherer et al. |
| 2005/0013529 A1 | 1/2005 | Chiu et al. |
| 2009/0161113 A1* | 6/2009 | Chen et al. ............... 356/477 |
| 2012/0057866 A1* | 3/2012 | McLaren et al. ............ 398/25 |

OTHER PUBLICATIONS

"International Application No. PCT/EP2010/003784, International Search Report mailed Aug. 12, 2010", 4 pgs.

"International Application No. PCT/EP2010/003784, Written Opinion mailed Aug. 12, 2010", 5 pgs.

* cited by examiner

OPTICAL SENSOR AND METHOD FOR DETECTING MOLECULES

PRIORITY CLAIM TO RELATED APPLICATIONS

This application is a national stage application under 35 U.S.C. §371 of PCT/EP2010/003784, filed Jun. 18, 2010, and published as WO 2011/000494 A1 on Jan. 6, 2011, which claims priority to European Application No. 09075286.6, filed Jul. 1, 2009, which applications and publication are incorporated by reference as if reproduced herein and made a part hereof in their entirety, and the benefit of priority of each of which is claimed herein.

The invention refers to an optical sensor having an optical waveguide various ring resonators, coupled optically to the waveguide, according to the preamble of the main claim and it also refers to a method for detecting molecules of at least one substance by means of such a sensor.

In the publication U.S. Pat. No. 7,145,660 B2, such optical sensors are described, in which the respective ring resonators can also be equipped with a device for adjusting resonance frequencies of the respective ring resonator. These known sensors are suitable for examining a specific variable to be measured which can be for example a pressure, a temperature or the presence or absence of molecules of a specific chemical compound. To this end, a measurement implemented with these sensors makes use of the influence of the variable to be measured upon the optical length of one of the ring resonators which has the consequence that the resonance frequencies of this ring resonator shift, which in turn can be detected by detecting light coupled out of the waveguide.

However, disadvantageously, the sensors known from the mentioned state of the art enable the examination/determination of a single variable to be measured only due to the fact that the ring resonator serving as sensor element is configured in such a way that its optical properties depend precisely upon this variable to be measured, for example by a coating with a specific chemically active substance, which allows molecules of a specific substance to be selectively immobilized at the surface.

However, it would be desirable for many applications to be able to examine similar but at the same time different variables. In particular, a sensitive detection of the presence or absence of molecules of specific compounds is of great importance in many fields, for example in medicine, biology, in environmental monitoring or in general for detecting dangerous substances, such as bacteria or toxic molecules in the air, in bodies of water or in other media (i.e. gases or liquids).

It is therefore the objective of the invention to develop a comparable sensor which enables, with as little effort as possible, the simultaneous determination of different variables of interest such as, for example, the presence or absence of different molecular species or groups of compounds. Furthermore, the invention aims at proposing a correspondingly simple detection method which allows the simultaneous detection of different molecular species or enables the detection of one specific type of molecule with particularly high accuracy.

This objective is achieved according to the invention by an optical sensor having the characterizing features of the main claim in conjunction with the generic features of the main claim and also by a method which exhibits the features of claim 12. Advantageous embodiments and further developments of the invention can be accomplished based upon the features of the sub-claims.

An optical sensor in compliance with the invention has therefore an optical waveguide into which light can be fed, a light-sensitive element for detecting light coupled out of the waveguide, and also various ring resonators. The ring resonators are optically coupled to the mentioned waveguide and, with the exception of at most one of the ring resonators, each of them has a device for adjusting resonance frequencies of the respective ring resonator and/or of a coupling between the ring resonator and the waveguide. Furthermore, at least two of the ring resonators have different optical lengths in their initial state and are disposed for having their resonance frequencies shifted by means of different variables to be measured and which are specific for each of these ring resonators. The variables to be measured can, in particular, be given by a presence or absence of molecules of a specific compound or group of compounds, by a temperature or by a pressure. In these cases, the term "initial state" of one of the ring resonators shall denote a state in which the ring resonators are in contact with none of the mentioned molecules, subjected to no external pressure or have a temperature not deviating from a temperature of the other ring resonators, respectively.

The coupling required according to the invention between the ring resonators and the optical waveguide can be achieved for example by a sufficiently small spacing between the respective ring resonator and the waveguide which extends preferably tangentially thereto and makes possible an overlap of evanescent fields by modes propagating in the ring resonators and in the waveguide. The ring resonators can be provided, in particularly simple embodiments of the invention, by circular closed waveguides, the different optical lengths of the ring resonators in the basic state then being able to be produced simply by different circumferential lengths of the ring resonators.

It becomes possible by means of the proposed measures to examine a plurality of variables to be measured at the same time because a change in each of the variables to be measured results in a shift of resonances of the ring resonator which reacts sensitively to this measured variable, this shift being able to be detected by the light-sensitive element for detecting the light coupled out of the waveguide and, thereby, the ring resonator causing the shifted resonances being able to be identified.

In the case of a preferred embodiment of the invention which is suitable for detecting different chemical substances or for particularly accurate detection of a chemical substance, the at least two ring resonators, which were described above as disposed for having their resonance frequencies influenced by variables to be measured, each have respectively one sensitive region which is provided with an active layer which is different for each of these ring resonators for selective immobilization or adsorption of one or more substances to be detected. The sensitive regions can possibly extend over the entire respective ring resonator. The active layer can be formed in each case for example from a molecularly imprinted polymer in order to have the required selective property and in general can be provided by an antibody for the substance to be detected. If the ring resonator provided with this active layer comes into contact with molecules of the corresponding substance, accumulation or immobilization of these molecules is the result, whereby, as a result of the immediate proximity thereof to the ring resonator, the optical length of the ring resonator is at least slightly changed, which in turn results in a shift in the resonance frequency of this ring resonator. Primarily, the sensor is, therefore, then suitable for simultaneous selective detection of molecules of different compounds or groups of compounds. Alternatively or additionally, the selectivity of a sensor which is intended to be able to detect the presence of molecules of only one specific compound or group of compounds can be increased by the proposed measures. This can be done by choosing the active layers of the different ring resonators such that the different groups of compounds which can accumulate on these active layers overlap such that an intersection contains only the compound or group of compounds to be detected.

In the case of the proposed method, correspondingly molecules of at least one substance are detected by means of a sensor of the described type by feeding light into the waveguide of the sensor, bringing a fluid to be examined in contact with at least two of the ring resonators of the sensor, and evaluating an output signal of the light-sensitive element as a function of the wavelength. A shift of resonances in the output signal caused by the fluid is detected and the ring resonator to which this shift can be attributed is identified by varying (modulating) the resonance frequencies of the ring resonators and/or their coupling to the waveguide with different time dependencies which are specific for each of the ring resonators and by determining which of these time dependencies is correlated with the shifted resonances. To this end, varying the resonance frequencies or the coupling of the ring resonators to the waveguide can be effected by a time-dependent actuation of the mentioned devices for adjusting the resonance frequencies or couplings.

Since the resonances of precisely one of the ring resonators can be assigned to said ring resonator even without modulation if the remaining ring resonators are identified by variation or modulation of their resonance frequencies and/or their coupling to the waveguide, it is sufficient if all but one of the ring resonators are equipped with a device for modulation and are modulated in the described method. Irrespective thereof, an optical circuit forming the sensor can, of course, possibly also comprise further ring resonators without a corresponding modulation device, which can serve for purposes other than those described here.

The devices for adjusting the resonance frequencies of the ring resonators or for adjusting the couplings between the respective ring resonator and the waveguide can be produced in a particularly simple manner with the help of heating elements, for example heating wires or heating layers, for rapid setting and adjustment of temperatures of the ring resonators or with the help of electrical contacts for applying an electrical field to the respective ring resonator. Then a dependency of an effective refractive index of the respective ring resonator upon a temperature or upon an external electrical field can be used for setting the resonance frequency. As long as such a heating element or such electrical contacts are situated in the immediate vicinity of a coupling range between ring resonator and waveguide, also the coupling between ring resonator and waveguide can consequently be influenced, alternatively or additionally.

Thus, the mentioned devices can, in particular, be configured for varying an effective refractive index of the respective ring resonator. In the case of a circular shape of the ring resonator, the latter then has an optical length of $2\pi R n$, R standing for a radius and n for the effective refractive index. The resonance frequencies are then defined by the condition that $N\lambda$ must correspond to the optical length of the ring resonator, N defining any natural number and $\lambda$ the vacuum wavelength associated with the respective resonance frequency—i.e. the resonance wavelength.

In order to allow an evaluation of the sensor in the manner described previously in the example of the method for detecting molecules, the sensor can be equipped with at least one control unit for the devices for adjusting the resonance frequencies, which is configured for modulating the effective refractive indices of the ring resonators with different time dependencies which are specific respectively for each of these ring resonators. In particular, the control unit can be configured to modulate the refractive indices of the ring resonators periodically with different modulation frequencies. In order to identify the ring resonator to which a shift of resonance frequencies can be attributed, the devices assigned to the different ring resonators for adjusting the resonance frequencies or the couplings between ring resonators and waveguide can, therefore, in particular be actuated periodically with different frequencies—or alternatively simply successively.

It is particularly advantageous if under the ring resonators of the sensor at least one reference resonator (preferably more than one reference ring) is arranged which has resonance frequencies which are independent of the variables to be measured and, therefore, remains unaffected by a change in the measured variables. The resonances in the output signal caused by the reference resonator can then be used as references with reference to which a shift in the other resonances is determined so that an absolute determination of the resonance frequencies, which can be produced only with additional complexity, becomes superfluous. In this way, a particularly accurate evaluation of the sensor becomes possible without determination of absolute values of the resonance frequencies, in particular when the sensor has two such reference resonators of different optical length.

In order that the output signal of the light-sensitive element, instead of which of course also a plurality of light-sensitive elements can be used, can be evaluated as a function of wavelength, the sensor can have a monochromatic light source exhibiting a tunable wavelength for coupling light into the waveguide. This can, for example, be a tunable laser. This light source can preferably be tuned over a wavelength range which comprises at least one resonance wavelength of each of the ring resonators in order that an effect of variables to be measured on each of the ring resonators can be detected. Then the output signal can be evaluated as a function of the wavelength by tuning the light fed into the waveguide over a wavelength range which comprises one resonance wavelength or also a plurality of resonance wavelengths of each of the ring resonators.

In order to avoid that a ring resonator, to which a shift of a resonance frequency or resonance wavelength can be attributed, cannot be identified because several resonances are superimposed, it can be provided that light of two different polarizations is fed into the waveguide of a preferably single-mode design and that the output signal is evaluated independently for each of these polarizations, since it is improbable that such a superimposition of resonances caused by different ring resonators occurs in both polarizations.

In an advantageous embodiment in which the sensor shows particularly high sensitivity, a second waveguide can be provided, which, together with the first-mentioned waveguide of the sensor, forms a Mach-Zehnder interferometer. The first-mentioned waveguide and the second waveguide can then be coupled to each other, for example by a 3 dB coupler in the propagation direction in front of and behind the ring resonators respectively. In this case, the resonances can be particularly well detected when tuning the light source because these resonances do not influence merely an intensity of the light emerging from the first-mentioned waveguide but also a phase of a wave corresponding to this light, and because a change in this phase can be detected easily and accurately with a Mach-Zehnder interferometer.

A particularly accurate evaluation is possible with a sensor of the last-mentioned type if both the first-mentioned waveguide and the second waveguide are coupled optically to respectively one light-sensitive element and if a difference amplifier is provided for evaluating output signals of these light-sensitive elements. In this case, the light-sensitive elements should be disposed preferably at one end of the respective waveguide. In this case, the light-sensitive elements act as so-called balanced detectors which are evaluated by a differential analysis. However, a measurement at the output of only one of the waveguides suffices so that, alternatively, merely a single light-sensitive element can be provided at the output of only one of the waveguides.

Preferably, in the case of a sensor of the just-described type, the first-mentioned waveguide or the second waveguide is equipped with a phase shifter which can be realized for example by a heating strip. The sensitivity of the sensor can then be increased by adjusting a relative phase between light components emerging from both waveguides by a corresponding actuation of the phase shifter—preferably already before a measurement to be performed with the sensor—such that changes of resonance wavelengths are placed respectively in a region of a steep edge so that a small phase shift results in a large change in the output signal.

Sensors of the proposed type can be designed advantageously compactly and robustly by producing at least the waveguide or the waveguides and the ring resonators in planar technology on a common substrate, e.g. a chip. In this case, waveguide cores both of the first-mentioned waveguide and of the ring resonators and possibly of the second waveguide can be produced for example by ribs or by doping of regions forming waveguide cores. Heating elements or electrodes which can serve as devices for adjusting resonance frequencies of the ring resonators or as phase shifters can be produced then for example by applying thin conducting layers.

In particular in cases in which the number of measuring points, i.e. the number of ring resonators to be measured, is intended to be increased significantly above approx. 10 to 20, it can be advantageous if the sensor has at least one additional waveguide which is coupled optically to at least one light-sensitive element and also in turn a plurality of additional ring resonators which are coupled optically to the additional waveguide and, in each case, equipped with a device for adjusting resonance frequencies, also at least some of the further ring resonators having different optical lengths in an initial state and being designed to have their resonance frequencies influenced by means of different variables to be measured which are specific for each of these ring resonators. The sensor can then have for example a matrix form with extensively parallel-extending waveguides, in the course of which the ring resonators are disposed in the immediate vicinity of the respective waveguide. In order to feed light into the various waveguides, for example a power divider can be used, which can be configured with the waveguides on a common substrate or as a fiber power divider.

Embodiments of the invention are explained subsequently with reference to FIGS. 1 to 3.

Figure 2:
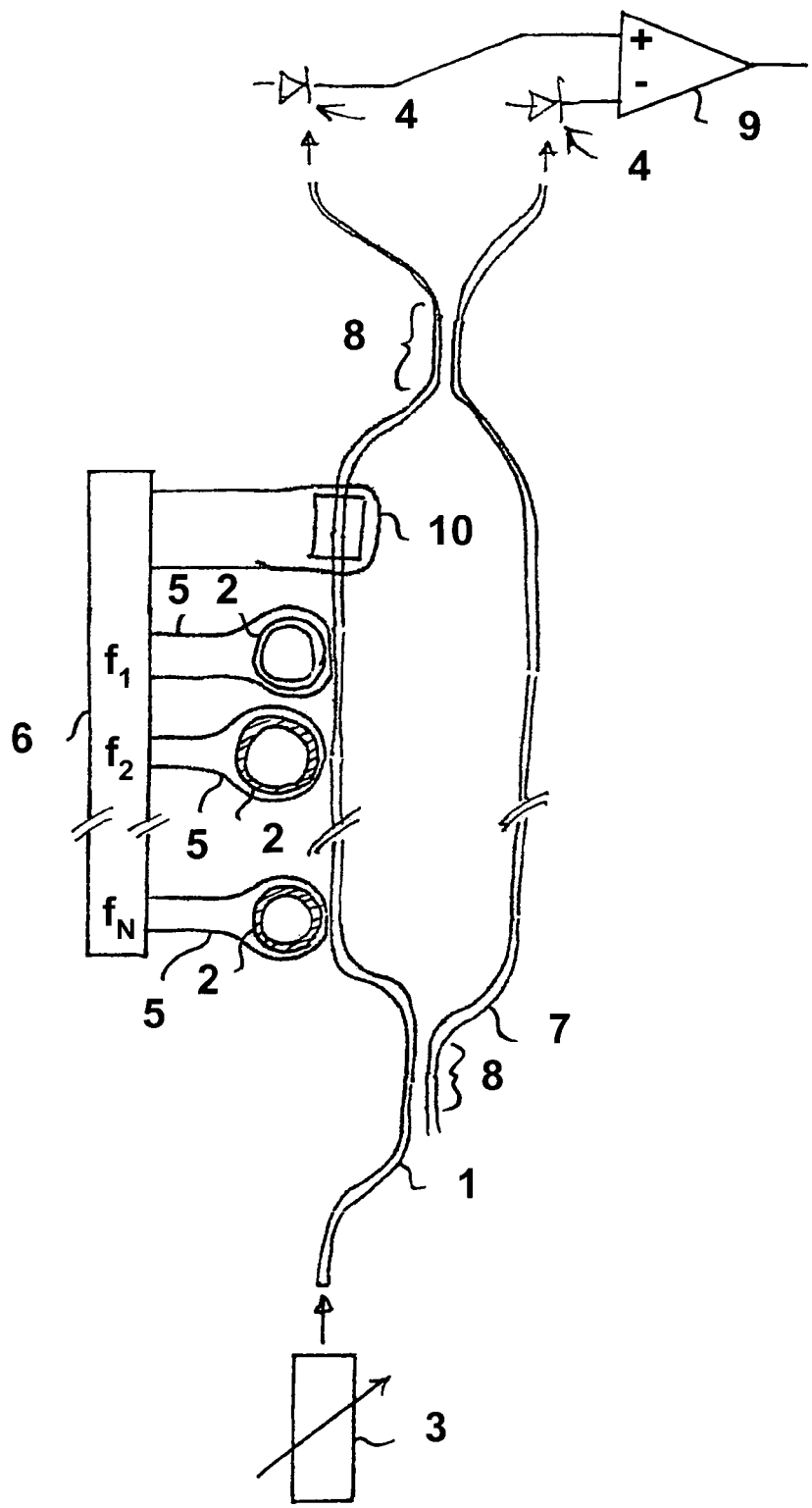
Figure 3:
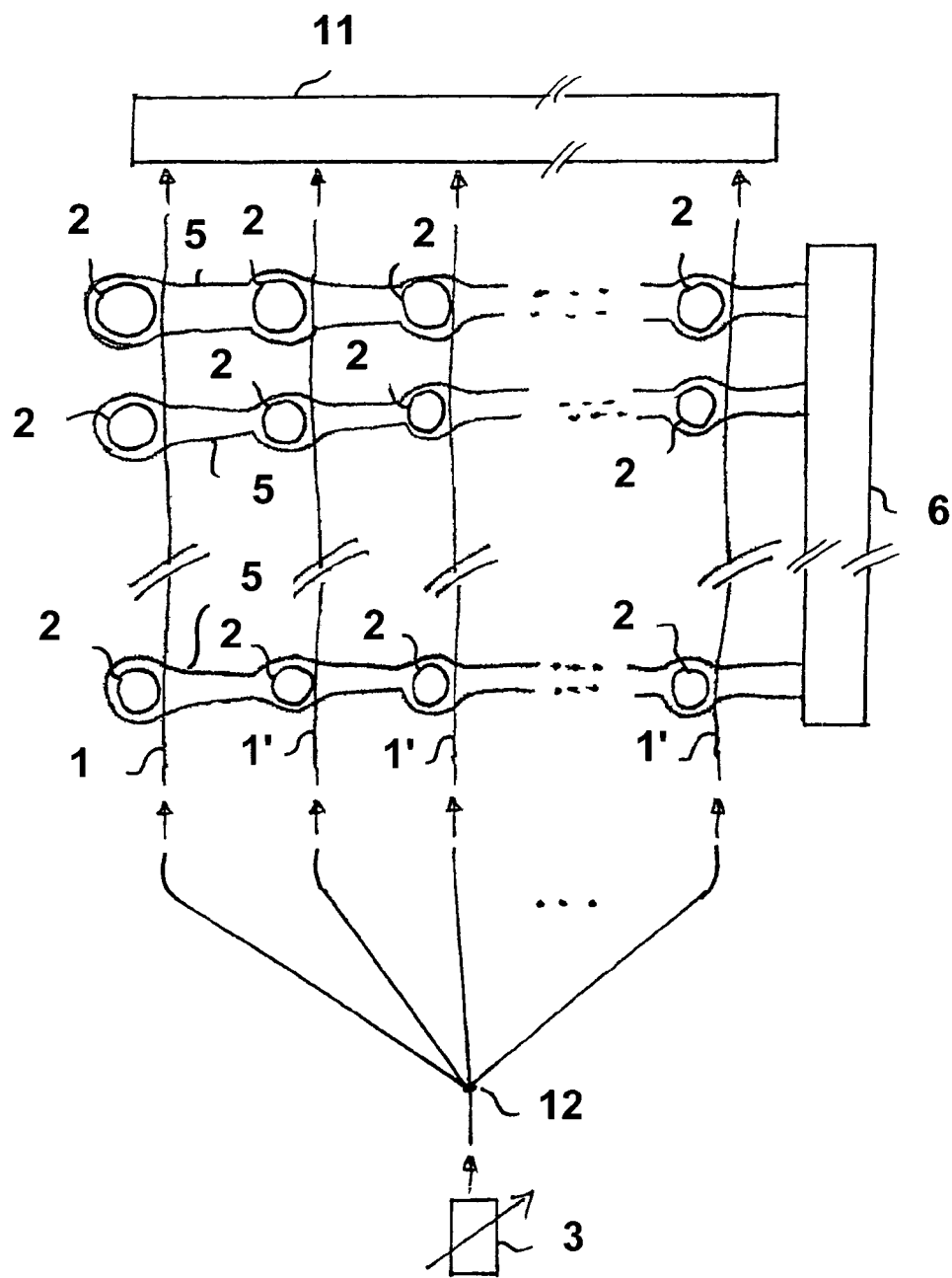

FIG. 1 is a top view of an optical sensor in a first embodiment of the invention, FIG. 2 is a top view of an optical sensor in a second embodiment of the invention and FIG. 3 is a top view of an optical sensor in a third embodiment of the invention.

In FIG. 1, a top view of an optical sensor is represented, which is, as are the embodiments of FIGS. 2 and 3, realized as an integrated optical circuit in planar technology on a chip-like substrate. Here, some components of this integrated optical circuit are illustrated merely schematically.

The optical sensor of FIG. 1 has a first waveguide 1, which extends in a straight line, and also a large number of optical ring resonators 2, which are configured as circular closed waveguides and which are coupled optically to the waveguide by choosing a spacing between the ring resonators 2 and the first waveguide 1, which extends tangentially thereto, so small that evanescent fields of modes which propagate in the first waveguide 1 and in the ring resonators 2 overlap. At a first end of the first waveguide 1, a light source 3, which is a tunable laser, is arranged for feeding light into the first waveguide 1. At a second end of the first waveguide 1, a light-sensitive element 4 which acts as photodetector for detecting light coupled out of the first waveguide 1 is arranged. Both the first waveguide 1 and the waveguides which form the ring resonators 2 have, in each case, a waveguide core which can be produced for example by a rib disposed on the substrate and separated from the latter by an optical buffer layer or by doping of the substrate manipulating the refractive index of a substrate material.

The ring resonators 2 differ from each other respectively by different radii and circumferential lengths so that they also have different optical lengths and therefore different resonance frequencies or resonance wavelengths. In addition, each of the ring resonators 2 has a device 5 for varying the resonance frequencies of the respective ring resonator 2, which device 5 is given by a thin layer serving as heating element. The heating elements of the devices 5 can be actuated by a control unit 6 such that the temperature-dependent effective refractive indices of the ring resonators 2 are modulated with different time dependencies which are specific respectively for each of the ring resonators 2. In particular, the effective refractive indices of the waveguides forming the ring resonators 2 and hence their optical lengths are modulated periodically with different frequencies $f_1$ to $f_N$. A variation in the optical lengths of the ring resonators 2 by this modulation thereby remains however substantially smaller than the difference between the optical lengths of the pairwise different ring resonators 2. Also the strength of the optical coupling between the respective ring resonator 2 and the first waveguide 1 is likewise varied at least slightly by the actuation of the devices 5. In the case of a modification of the embodiment described here, the devices 5, instead of heating elements, can also have electrodes for applying electrical fields to the waveguides forming the ring resonators 2 in order to use, instead of a temperature dependency of the refractive indices, their dependency upon an external electrical field.

With the exception of two of the ring resonators 2, which can be, for example, the smallest ring resonator 2, shown at the very top in FIG. 1, and the largest ring resonator 2, shown at the very bottom in FIG. 1, and which serve as reference resonators, the ring resonators 2 are, in each case, provided with an active layer which is different for each of these ring resonators 2 for selective accumulation or immobilization of molecules of a specific chemical compound or group of compounds. These active layers, which are illustrated in FIG. 1 by hatched areas, preferably cover an upper side of the respective ring resonator and form a sensitive region of the ring resonator 2. If this sensitive region comes in contact with molecules of the compound or of the group of compounds which the active layer allows to immobilize, these molecules accumulate in the immediate vicinity of the waveguide core of the respective ring resonator 2. As a function of their concentration, they consequently change the effective refractive index and hence the optical length of this ring resonator 2. This results in turn in the resonance frequencies or resonance wavelengths of the relevant ring resonator 2 being shifted at least slightly. The presence or absence or the concentration of the mentioned molecules in a fluid brought in contact with the ring resonator 2 thus defines a variable to be measured by means of which the resonance frequencies and resonance wavelengths of the ring resonator 2 provided with the corresponding active layer can be influenced.

The two ring resonators 2 which form the reference resonators are in contrast designed to be encapsulated so that their resonance frequencies are independent of the variables to be measured.

By means of a corresponding choice of the active layers on the ring resonators 2, the optical sensor can be equipped for simultaneous detection of molecules of different substances or for particularly accurate detection of a specific substance, in particular for sensitive detection of dangerous substances, such as bacteria or toxic molecules in the air or in bodies of water. In the case of an advantageously simple method for detecting such molecules of at least one substance, light is fed into the first waveguide 1 by the light source 3 and a fluid to be examined, i.e. for example air or water, is brought in contact with the ring resonators 2 of the sensor. At the same time, an output signal of the light-sensitive element 4 is evaluated as a function of wavelength by tuning the light fed into the waveguide 1 over a wavelength range which is so large that it includes at least one resonance wavelength of each of the ring resonators 2. A shift of resonances in the output signal which is caused by the fluid and which can be attributed to an immobilization or accumulation of molecules on the active layers of the ring resonators 2, which allow precisely these molecules to accumulate or to be immobilized or adsorbed, is detected by evaluation of the mentioned output signal in which the resonances can be detected as intensity minima. The ring resonator 2 or ring resonators 2 to which this shift can be attributed is or are identified by varying the resonance frequencies of the ring resonators 2 and, within specific limits, also coupling of the ring resonators 2 to the waveguide 1 by means of the devices 5 with different time dependencies which are specific, in each case, for precisely one of the ring resonators 2, and by determining which of these time dependencies is correlated with the shifted resonances. To this end, the devices 5 of the various ring resonators 2 can be actuated for example periodically with the different frequencies $f_1$ to $f_N$, which leads to a periodic shift in the resonances with precisely the frequency $f_i$ which can be attributed to a specific ring resonator 2, with which frequency $f_i$ this ring resonator 2 or the optical length thereof is modulated. Consequently, the resonator shifts caused by the fluid are in each case unequivocally assigned to a single one of the ring resonators 2 designed as microrings by changing periodically, during the measurement, the optical length of the ring resonators 2 such that the change in resonance wavelength associated with the respective ring resonator 2 can be determined unequivocally by coherent detection. Instead of a simultaneous modulation of all ring resonators 2 with different frequencies $f_1$ to $f_N$, the ring resonators 2 can also be modulated successively by actuating the devices 5 of the ring resonators 2 successively.

If a measurement of the described type is implemented not only after the ring resonators 2 have been brought in contact with the fluid and the modules to be detected have accumulated or have been adsorbed on the various ring resonators 2 but also before, the presence of the molecules to be detected can be easily recognized in that the associated resonances, i.e. the resonances which can be attributed to the ring resonators 2 on which the molecules to be detected were able to accumulate, have shifted, the size of the shift providing at least a relative value for the number of accumulated molecules, i.e. for a concentration of these molecules in the examined fluid.

As a result of the fact that the two reference resonators are not provided with an active layer (or adhesive layer) so that the resonances associated with these reference resonator are not shifted, the resonances which are caused by the reference resonators and which can be detected like the other resonances in the output signal of the light-sensitive element 4 measuring the transmission through the first waveguide 1 can serve as calibration marks. These resonances or calibration marks make it possible to identify shifts of all resonances, e.g. by changes in ambient temperature. Therefore in particular there is no requirement to know exactly the respectively used wavelengths of the light. It need merely be ensured that the entire wavelength range over which the light source 3 is tuned is passed through at a uniform speed so that, via the structures of the reference resonators, i.e. via the resonances to be attributed to the reference resonators, and via the time, relative shifts of all other resonances can be determined unequivocally.

The effective refractive index of the ring resonators 2 upon which their optical lengths depend shows a pronounced dependency upon the polarization of the light which is coupled into the polarization-maintaining single-mode waveguide 1 and from the latter into the ring resonators 2, which are likewise configured to be single-mode. A differentiation between TE- and TM-modes can thereby be made. If the described analysis is implemented both with TE- and TM-polarized light, advantageously two sets of measuring data are obtained which are independent of each other and can be used for a reduction of remaining measuring uncertainties. This applies in particular when the structures or resonances to be measured for one of the polarizations are situated by chance in a spectral range in which many structures overlap, which can make separation of the measuring signals associated with the different ring resonators difficult.

The described method, which is simple in its principle and which has the potential to be transferred even to hand-held devices, requires in particular no temperature stabilization of the optical sensor configured as measuring chip and enables, in the described manner, a label-free in situ measurement. A simultaneous measurement on ring resonators 2 provided possibly in large numbers is thereby possible. This is of importance for example if the presence of a specific molecule must be determined with high reliability. Then a sufficiently large number of microrings which form the ring resonators 2 can be coated with the corresponding antibody which then forms the respective active layer and a likewise sufficiently large number of microrings can be configured to be uncoated or not selectively coated and used as reference resonators for comparing with the ring resonators 2 serving as sensor elements. The method thereby requires no spectrally resolved detection, e.g. via a spectrometer, and also no radiation source with an exactly known emission wavelength as light source 3.

Another embodiment of an optical sensor of a corresponding mode of operation is represented in FIG. 2. Here and in the description of the following embodiment of FIG. 3, features already described above are provided with identical reference numbers and are no longer explained in detail.

The sensor shown in FIG. 2 has, in addition, a second waveguide 7 which, together with the first waveguide 1, forms a Mach-Zehnder interferometer. In the propagation direction of the light coupled into the first waveguide 1 from the light source 3, the two waveguides 1 and 7, which extend essentially parallel to each other, are coupled to each other in front of and behind the ring resonators 2 respectively by a directional coupler 8 which is configured as 3 dB coupler. An output both of the first waveguide 1 and of the second waveguide 7 is coupled optically respectively to a light-sensitive element 4, a difference amplifier 9 being provided for evaluating output signals of these light-sensitive elements 4. An output signal of the difference amplifier 9 consequently depends very sensitively upon a relative phase position between a wave component propagating in the first waveguide 1 and one in the second waveguide 7 in the range of the second directional coupler 8 behind the ring resonators 22. Since a resonance of any of the ring resonators 2 influences not only an intensity of the light component propagating through the first waveguide 1 but also the phase position thereof, the resonances can be detected in the same way by evaluation of the output signal of the difference amplifier 9 as in the case of the above-described embodiment by evaluation of the output signal of the merely one light-sensitive element 4 there. However, also in the case of the arrangement shown in FIG. 2, one of the two light-sensitive elements 4 could be omitted and a measurement could be undertaken at the output of only one of the two waveguides 1 and 7.

In the course of the first waveguide 1, a phase shifter 10 is arranged in the sensor of FIG. 2 which can be configured similarly to the devices 5 of the ring resonators 2 and with which the phase position of the light component propagating through the first waveguide 1 can be adjusted. In the present embodiment, this phase shifter 10 is realized by a heating strip which allows an effective refractive index of the first waveguide to be manipulated in the range of the phase shifter 10. The phase shifter 10 could similarly also be fitted on the second waveguide 7. In the case of the detection method performed with the sensor of FIG. 2, which otherwise corresponds to the previously described method, now a relative phase position between the light components emerging from the two waveguides 1 and 7 is adjusted for sensitivity increase before the measurement such that changes in resonance wavelengths are placed respectively in a region of a steep edge of the output signal of the difference amplifier 9. By means of the partial piece of the—in the present example—first waveguide 1 supplied with the heating strip, the phase relation at the output of the Mach-Zehnder interferometer is adjusted such that a sensitivity of the sensor is maximized.

If the number of measuring points, i.e. the number of ring resonators 2 to be measured, is intended to be significantly increased, a parallel arrangement of a plurality of waveguides with ring resonators 2 which are configured in the described manner and respectively coupled to these waveguides is recommended. A correspondingly configured optical sensor is shown in FIG. 3, recurrent features there being provided again with the same reference numbers. In addition to the first waveguide 1, this sensor has a plurality of further waveguides 1' which extend parallel to the first waveguide 1, also each of the further waveguides 1' being coupled optically to a respective plurality of ring resonators 2 which in turn likewise have, in each case, a device 5 for adjusting resonance frequencies of the respective ring resonator 2. Also the ring resonators 2 coupled to the further waveguides 1' have, already in an initial state or ground state, different optical lengths which are caused by different radii of the ring resonators 2 and are configured similarly to the ring resonators 2 of the previously described embodiments for having their resonance frequency influenced by means of different measured variables which are specific for each of these ring resonators 2. Detection of optical output signals emerging from the waveguides 1 and 1' is effected in this case with the help of a detector array 11 which comprises a light-sensitive element for each of the waveguides 1 and 1'. In order to feed light into the waveguides 1 and 1', the sensor of FIG. 3 has a passive power divider 12 which can be disposed on the same chip or substrate as the waveguides 1 and 1' and the ring resonators 2 or can be realized in front of the chip by a fiber power divider. In the last-mentioned case, a fiber bundle forming the power divider 12 can be disposed at inputs of the waveguides 1 and 1' with a single adjustment for feeding light into these waveguides 1 and 1'.

In a further modification, again a reference waveguide corresponding to the second waveguide 7 of FIG. 2 can be provided finally also for each of the waveguides guides 1 and 1' so that the sensor has a plurality of Mach-Zehnder interferometers which are disposed parallel to each other and coupled to ring resonators 2.

The invention claimed is:

1. An optical sensor, comprising:
   an optical waveguide into which light can be fed,
   at least one light-sensitive element for detecting light coupled out of the waveguide; and
   a plurality of ring resonators, the ring resonators being coupled optically to the mentioned waveguide and, with the exception of at most one of the ring resonators, each having a device for adjusting resonance frequencies of the respective ring resonator and/or of a coupling between the ring resonator and the waveguide,
   wherein said devices are equipped with a means for varying an effective refractive index of the respective ring resonator and wherein at least two of the ring resonators have different optical lengths in an initial state and are disposed for having their resonance frequencies influenced by different variables to be measured which are specific for each of these ring resonators,
   the sensor further comprising a control unit for the devices for adjusting the resonance frequencies of the ring resonators, the control unit being configured for modulating the effective refractive indices of the ring resonators with different time dependencies which are specific for each of these ring resonators.

2. The sensor according to claim 1, wherein each of the at least two ring resonators has a sensitive region which is provided with an active layer, the active layers being different for each of these ring resonators for selectively immobilizing of one or more substances to be detected.

3. The sensor according to claim 1, wherein the ring resonators comprise at least one reference resonator, the reference resonator having resonance frequencies which are independent of the variables to be measured.

4. The sensor according to claim 1, further comprising a light source exhibiting a tunable wavelength for coupling light into the waveguide.

5. The sensor according to claim 1, wherein the devices for adjusting the resonance frequencies of the ring resonators comprise a heating element or electrical contacts for applying an electrical field to the respective ring resonator.

6. The sensor according to claim 1, wherein the sensor comprises at least a second waveguide, the first-mentioned waveguide and the second waveguide forming a Mach-Zehnder interferometer.

7. The sensor according to claim 6, wherein each of the first-mentioned waveguide and the second waveguide is coupled optically to a light-sensitive element, the sensor further comprising a difference amplifier is provided for evaluating output signals of these light-sensitive elements.

8. The sensor according to claim 6, wherein the first-mentioned waveguide or the second waveguide is equipped with a phase shifter.

9. The sensor according to claim 1, wherein the sensor comprises at least one additional waveguide which is coupled optically to a light-sensitive element and various additional ring resonators which are coupled optically to the additional waveguide, each of the additional ring resonators being equipped with a device for adjusting their resonance frequencies, at least two of the additional ring resonators having different optical lengths in an initial state and being designed to have their resonance frequencies influenced by means of different variables to be measured which are specific for each of these ring resonators.

10. A method for detecting molecules of at least one substance by means of a sensor, the sensor comprising an optical waveguide, at least one light-sensitive element for detecting light coupled out of the waveguide and a plurality of ring resonators, the ring resonators being coupled optically to the waveguide and, with the exception of at most one of the ring resonators, each having a device for adjusting resonance frequencies of the respective ring resonator and/or of a coupling between the ring resonator and the waveguide, wherein at least two of the ring resonators have different optical lengths in an initial state and are disposed for having their resonance frequencies influenced by different variables to be measured which are specific for each of these ring resonators, the method comprising:

feeding light into the waveguide, bringing a fluid to be examined in contact with at least two of the ring resonators of the sensor and evaluating an output signal of the light-sensitive element which is evaluated as a function of wavelength, wherein evaluating the output signal comprises detecting a shift of resonances in the output signal caused by the fluid and identifying the ring resonator to which this shift can be attributed by varying the resonance frequencies of the ring resonators and/or their coupling to the waveguide with different time dependencies which are specific for each of the ring resonators and by determining which of these time dependencies is correlated with the shifted resonances.

11. The method according to claim 10, wherein the devices assigned to the different ring resonators for adjusting the resonance frequencies and/or the coupling between ring resonator and waveguide are actuated successively or periodically with different frequencies.

12. The method according to claim 10, wherein the output signal is evaluated as a function of wavelength by tuning the light fed into the waveguide over a wavelength range which comprises at least one resonance wavelength of each of the ring resonators.

13. The method according to claim 10, wherein light of two different polarizations is fed into the waveguide and the output signal is evaluated independently for each of these polarizations.

14. A method for detecting molecules of at least one substance by means of a sensor, the sensor comprising an optical waveguide, at least one light-sensitive element for detecting light coupled out of the waveguide and a plurality of ring resonators, the ring resonators being coupled optically to the waveguide and, with the exception of at most one of the ring resonators, each having a device for adjusting resonance frequencies of the respective ring resonator and/or of a coupling between the ring resonator and the waveguide, wherein said devices are equipped with a means for varying an effective refractive index of the respective ring resonators and wherein at least two of the ring resonators have different optical lengths in an initial state and are disposed for having their resonance frequencies influenced by different variables to be measured which are specific for each of these ring resonators, the sensor further comprising a control unit for the devices for adjusting the resonance frequencies of the ring resonators, the control unit being configured for modulating the effective refractive indices of the ring resonators with different time dependencies which are specific for each of these ring resonators, the method comprising:

feeding light into the waveguide, bringing a fluid to be examined in contact with at least two of the ring resonators of the sensor and evaluating an output signal of the light-sensitive element is evaluated as a function of wavelength, wherein evaluating the output signal comprises detecting a shift of resonances in the output signal caused by the fluid and identifying the ring resonator to which this shift can be attributed by varying the resonance frequencies of the ring resonators and/or their coupling to the waveguide with different time dependencies which are specific for each of the ring resonators and by determining which of these time dependencies is correlated with the shifted resonances.

* * * * *